(12) United States Patent
Liu

(10) Patent No.: US 11,006,673 B2
(45) Date of Patent: May 18, 2021

(54) ELECTRONIC CIGARETTE

(71) Applicant: Tuanfang Liu, Shenzhen (CN)

(72) Inventor: Tuanfang Liu, Shenzhen (CN)

(*) Notice: Subject to any disclaimer, the term of this patent is extended or adjusted under 35 U.S.C. 154(b) by 285 days.

(21) Appl. No.: 16/273,091

(22) Filed: Feb. 11, 2019

(65) Prior Publication Data

US 2019/0289913 A1 Sep. 26, 2019

(30) Foreign Application Priority Data

Mar. 24, 2018 (CN) .......................... 201820404148.5
Nov. 6, 2018 (CN) .......................... 201811310500.X

(51) Int. Cl.
*A24F 47/00* (2020.01)
*A61M 15/06* (2006.01)
*A61M 11/04* (2006.01)

(52) U.S. Cl.
CPC ......... *A24F 47/008* (2013.01); *A61M 11/042* (2014.02); *A61M 15/06* (2013.01); *A61M 2205/8206* (2013.01)

(58) Field of Classification Search
None
See application file for complete search history.

(56) References Cited

U.S. PATENT DOCUMENTS

| 10,582,728 | B2* | 3/2020 | Liu | A24F 40/70 |
|---|---|---|---|---|
| 2016/0183592 | A1* | 6/2016 | Liu | A24F 40/40 |
| | | | | 131/329 |
| 2019/0069598 | A1* | 3/2019 | Liu | A24F 40/46 |
| 2019/0289911 | A1* | 9/2019 | Liu | A61M 11/042 |
| 2019/0289912 | A1* | 9/2019 | Liu | A61M 15/06 |
| 2020/0113241 | A1* | 4/2020 | Liu | A24F 47/008 |
| 2020/0178614 | A1* | 6/2020 | Liu | A24F 47/008 |
| 2020/0196677 | A1* | 6/2020 | Liu | A24F 40/40 |
| 2020/0214359 | A1* | 7/2020 | Liu | A24F 7/00 |
| 2020/0297036 | A1* | 9/2020 | Liu | A24F 40/485 |
| 2020/0297037 | A1* | 9/2020 | Liu | A24F 1/32 |
| 2020/0315262 | A1* | 10/2020 | Liu | A24F 47/008 |
| 2020/0315263 | A1* | 10/2020 | Liu | H01M 2/1094 |
| 2020/0315264 | A1* | 10/2020 | Liu | A24F 40/10 |
| 2020/0359701 | A1* | 11/2020 | Liu | A24F 40/20 |
| 2020/0404980 | A1* | 12/2020 | Liu | A24F 47/008 |

* cited by examiner

*Primary Examiner* — Ross N Gushi
(74) *Attorney, Agent, or Firm* — Matthias Scholl P.C.; Matthias Scholl

(57) ABSTRACT

An electronic cigarette, including an atomizing assembly and a battery assembly. The atomizing assembly is disposed on the battery assembly. The atomizing assembly includes a mouthpiece cover, a mouthpiece, a first sealer adapted to seal the mouthpiece, an atomizing core, a connector, a first fixed seat adapted to fix the atomizing core, a seal ring adapted to seal the first fixed seat, a screwed ring, a regulating ring, a second sealer adapted to seal the regulating ring, a joint, an insulation ring, a second fixed seat adapted to fix the regulating ring, an e-liquid feeder including an e-liquid inlet, a funnel, a third sealer adapted to seal the funnel, a first spring, a fourth sealer adapted to seal the e-liquid inlet of the e-liquid feeder, and a sealing seat. The battery assembly includes screws, elastic sheets, an electrode holder, a button, output electrodes, a fifth sealer.

1 Claim, 5 Drawing Sheets

ELECTRONIC CIGARETTE

CROSS-REFERENCE TO RELAYED APPLICATIONS

Pursuant to 35 U.S.C. § 119 and the Paris Convention Treaty, this application claims foreign priority to Chinese Patent Application No. 201820404148.5 filed Mar. 24, 2018, and to Chinese Patent Application No. 201811310500.X filed Nov. 6, 2018. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND

This disclosure relates to an electronic cigarette.

Electronic cigarettes atomize nicotine-containing e-liquid.

Conventionally, the atomizing assembly fixedly communicates with the battery assembly. This increases the difficulty in replacing the atomization core. In addition, the atomizing core tends to slide out in the process of regulating the volume flow rate of the vapor. This increases the risk of unwanted leakage of the e-liquid.

SUMMARY

The disclosure provides an electronic cigarette.

Provided is an electronic cigarette, comprising an atomizing assembly and a battery assembly. The atomizing assembly is disposed on the battery assembly. The atomizing assembly comprises a mouthpiece cover, a mouthpiece, a first sealer adapted to seal the mouthpiece, an atomizing core, a connector, a first fixed seat adapted to fix the atomizing core, a seal ring adapted to seal the first fixed seat, a screwed ring, a regulating ring, a second sealer adapted to seal the regulating ring, a joint, an insulation ring, a second fixed seat adapted to fix the regulating ring, an e-liquid feeder comprising an e-liquid inlet, a funnel, a third sealer adapted to seal the funnel, a first spring, a fourth sealer adapted to seal the e-liquid inlet of the e-liquid feeder, and a sealing seat.

The battery assembly comprises screws, elastic sheets, an electrode holder, a button, output electrodes, a fifth sealer adapted to seal the output electrodes, second springs, fixed rings adapted to fix the output electrodes, a housing, a control plate, a support, and a battery cell.

The first sealer is disposed on the connector, and the connector is disposed in the mouthpiece; the mouthpiece cover is disposed on the mouthpiece; the joint is disposed in the insulation ring, and the insulation ring is disposed in the second fixed seat; the second sealer is disposed on the second fixed seat, and the regulating ring is disposed on the second sealer; the seal ring is disposed on and adapted to seal the first fixed seat; the screwed ring is disposed in the first fixed seat; the first fixed seat is disposed in the mouthpiece; the atomizing core is disposed on the second fixed seat, and the second fixed seat is connected to the first fixed seat.

The fourth sealer is disposed on the sealing seat, and the sealing seat is mounted on one end of the funnel; the third sealer and the first spring sleeve the funnel, and the funnel is inserted in the e-liquid feeder; the e-liquid feeder is disposed on the first fixed seat; the regulating ring comprises locating slots, and the second fixed seat comprises stop pins corresponding to the locating slots.

The control plate and the battery cell are disposed at two sides of the support, respectively; the support is disposed in the housing; the fifth sealer and the second springs are disposed on the output electrodes; the output electrodes are disposed on the electrode holder and are fixed by the fixed rings; the elastic sheets are disposed on the electrode holder and are fixed by the screws; and the button is disposed on the housing, and the electrode holder is disposed in the housing.

Advantages of the electronic cigarette according to embodiments of the disclosure are summarized as follows. The atomizing assembly communicates with the battery assembly via two elastic sheets disposed at two sides of the battery assembly. The two elastic sheets communicate with the first fixed seat of the atomizing assembly. This simplifies the dismantling of the electronic cigarette and facilitates the replacement of the atomizing assembly. In the process of loading the e-liquid, press down the funnel, and the e-liquid inlet of the funnel is elastically opened and exposed out of the e-liquid feeder. The e-liquid is injected via the e-liquid inlet. After the injection, the funnel is elastically withdrawn into the e-liquid feeder and is sealed by the fourth sealer and the sealing seat, and the e-liquid inlet is closely sealed in the e-liquid feeder, thus preventing the unwanted leakage of the e-liquid.

DETAILED DESCRIPTION

To further illustrate, embodiments detailing an electronic cigarette are described below. It should be noted that the following embodiments are intended to describe and not to limit the disclosure.

Figure 1:
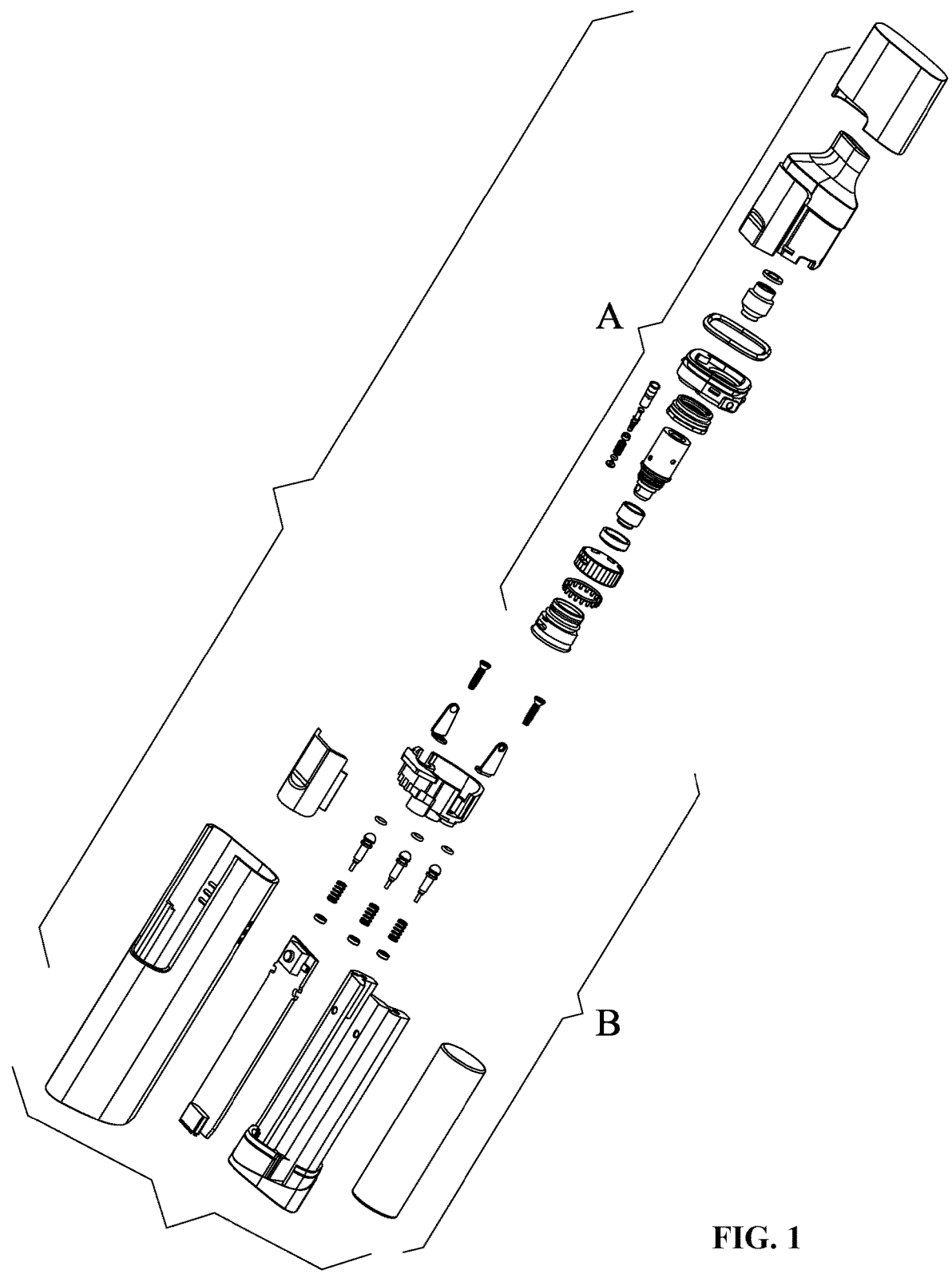
FIG. 1 is an exploded view of an electronic cigarette as described in the disclosure.
Figure 2:
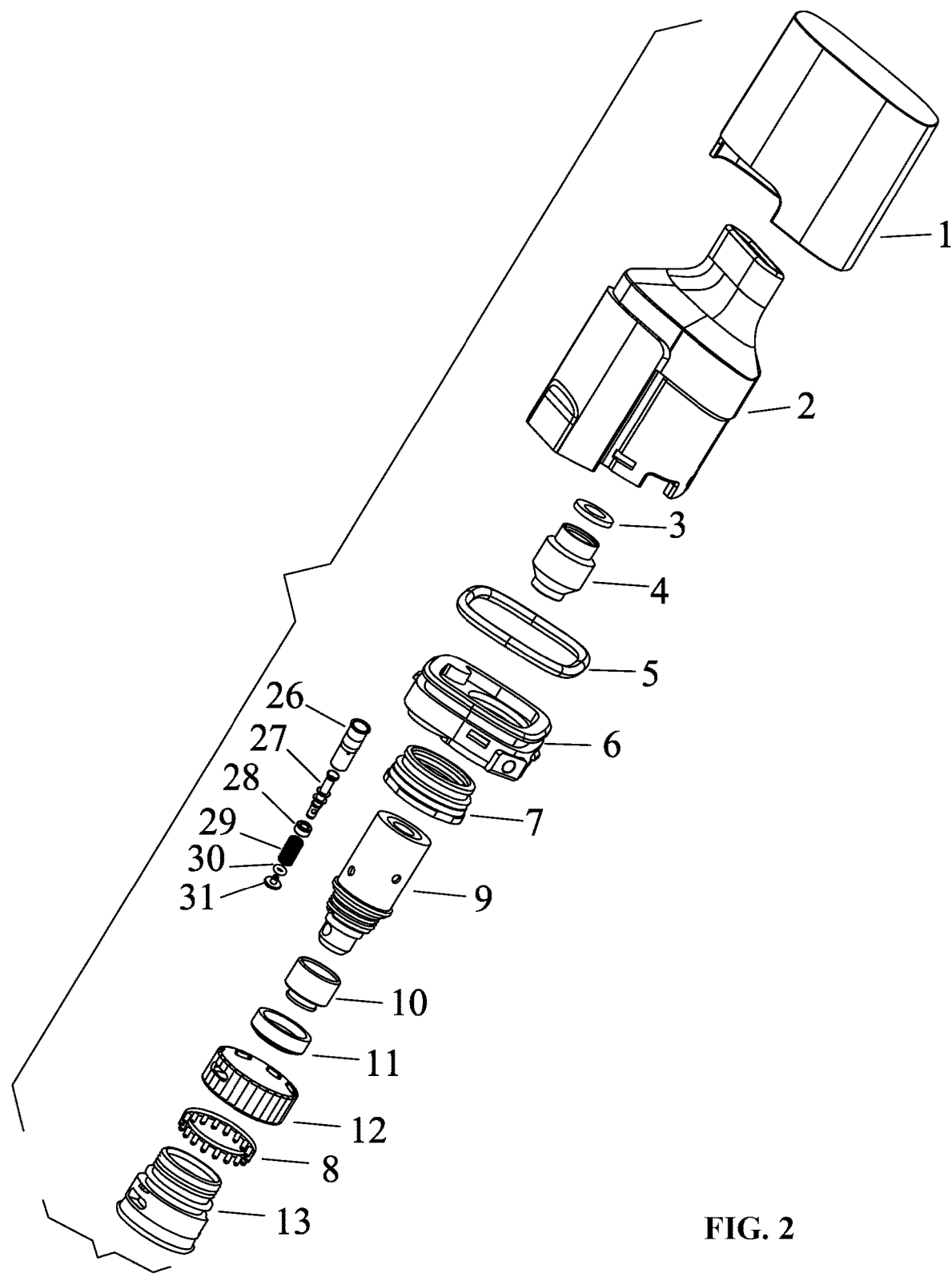
FIG. 2 is an exploded view of an atomizing assembly of an electronic cigarette as described in the disclosure.
Figure 3:
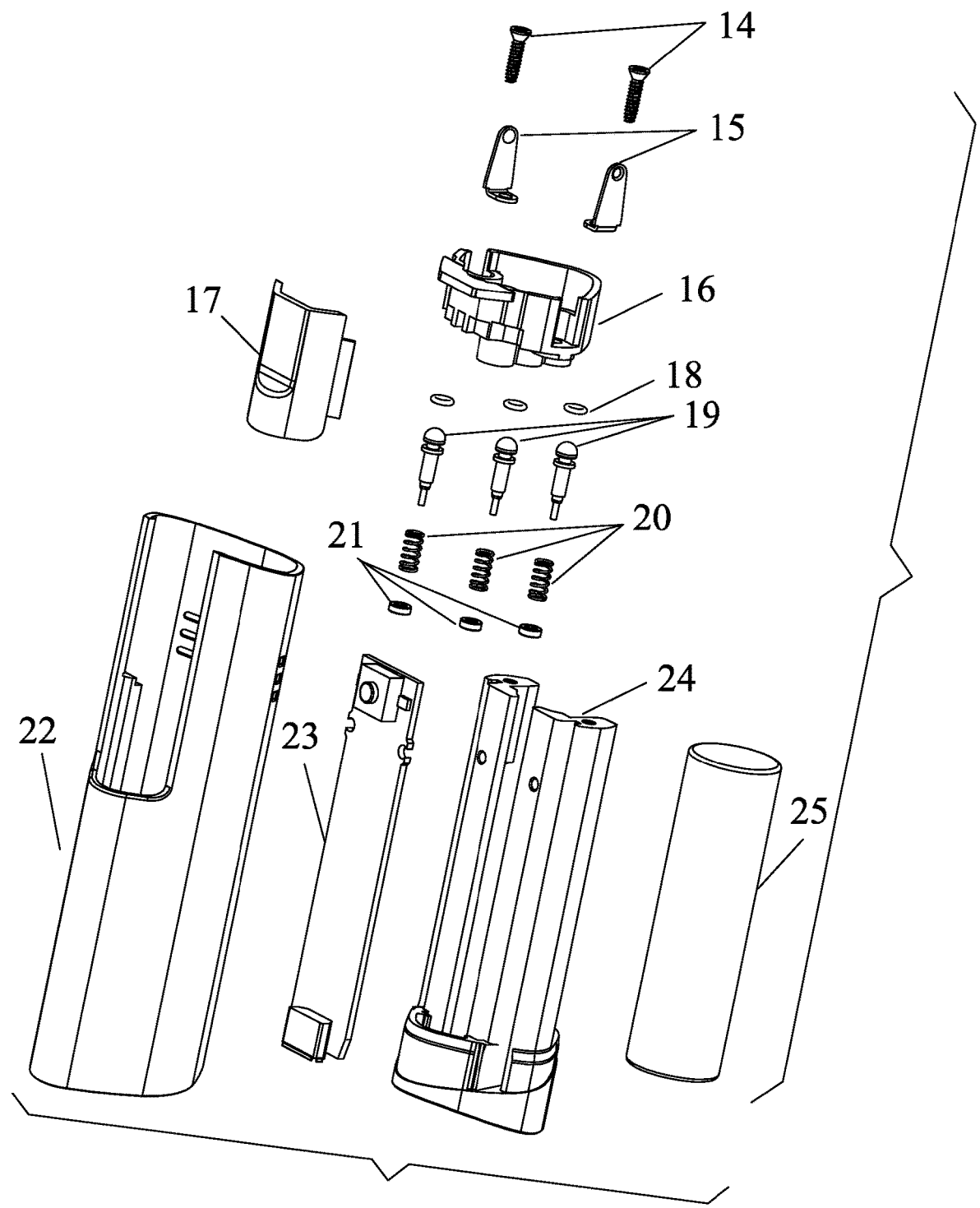
FIG. 3 is an exploded view of a battery assembly of an electronic cigarette as described in the disclosure.
Figure 4:
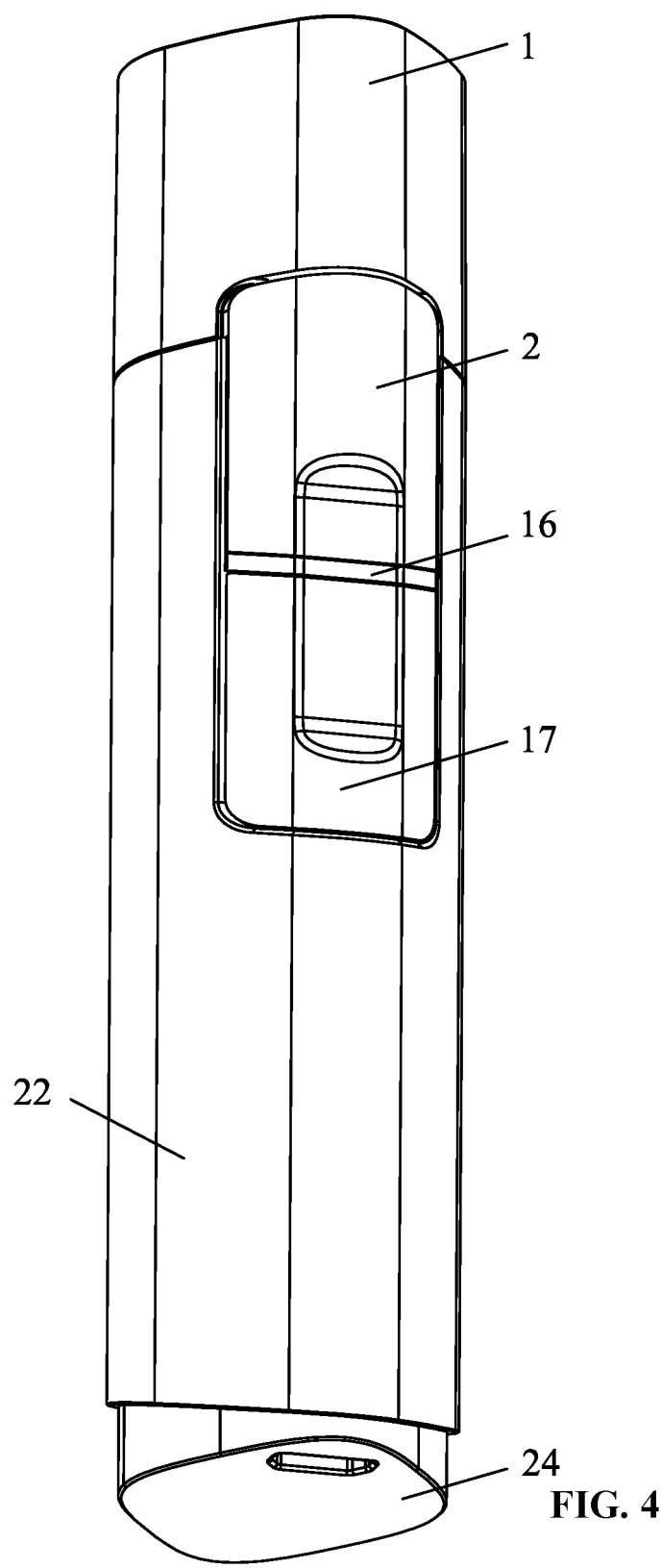
FIG. 4 is a stereogram of an electronic cigarette as described in the disclosure.
Figure 5:
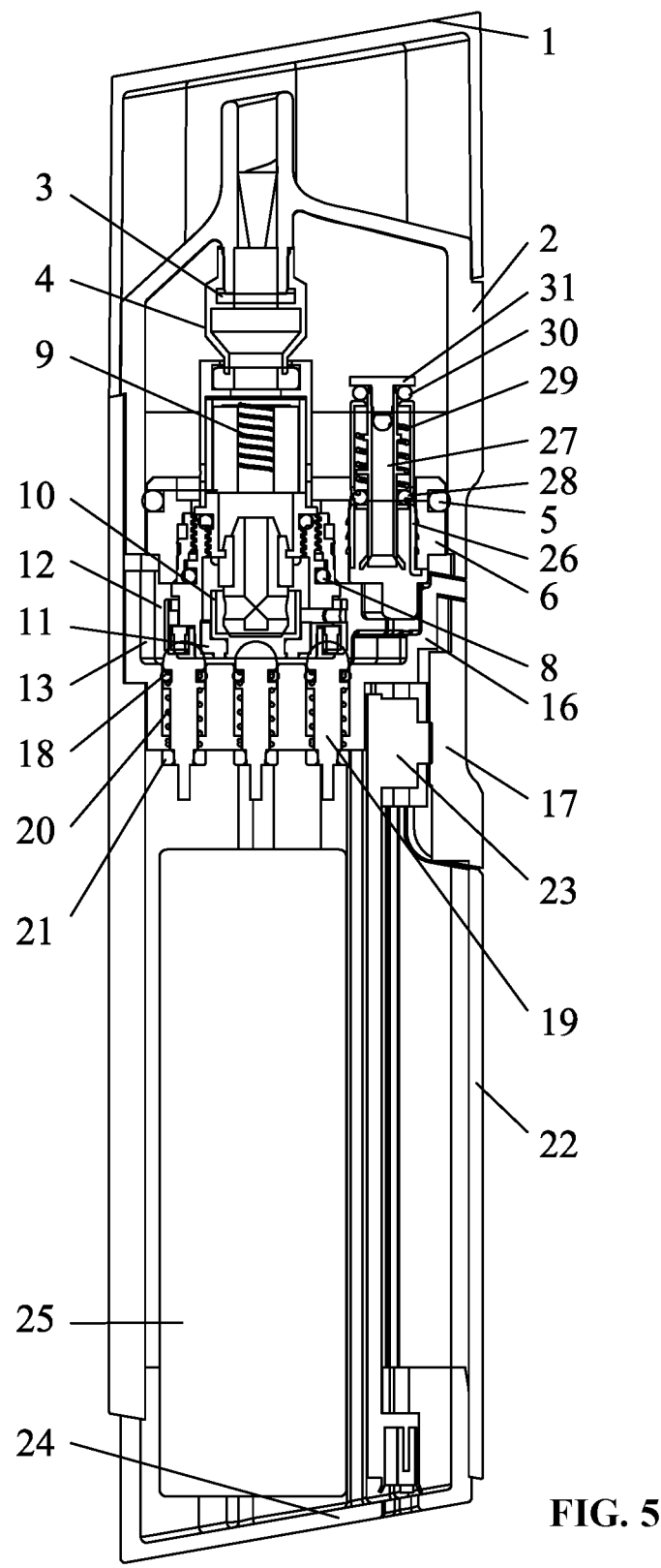
FIG. 5 is a sectional view of an electronic cigarette as described in the disclosure.

As shown in FIGS. 1-5, provided is an electronic cigarette, comprising: an atomizing assembly A; and a battery assembly B. The atomizing assembly A is disposed on the battery assembly B.

The atomizing assembly A comprises a mouthpiece cover 1, a mouthpiece 2, a first sealer 3 adapted to seal the mouthpiece 2, an atomizing core 9, a connector 4, a first fixed seat 6 adapted to fix the atomizing core 9, a seal ring 5 adapted to seal the first fixed seat 6, a screwed ring 7, a regulating ring 12, a second sealer 8 adapted to seal the regulating ring 12, a joint 10, an insulation ring 11, a second fixed seat 13 adapted to fix the regulating ring 12, an e-liquid feeder 26 comprising an e-liquid inlet, a funnel 27, a third sealer 28 adapted to seal the funnel 27, a first spring 29, a fourth sealer 30 adapted to seal the e-liquid inlet of the e-liquid feeder 26, and a sealing seat 31.

The battery assembly B comprises screws 14, elastic sheets 15, an electrode holder 16, a button 17, output electrodes 19, a fifth sealer 18 adapted to seal the output electrodes 19, second springs 20, fixed rings 21 adapted to fix the output electrodes 19, a housing 22, a control plate 23, a support 24, and a battery cell 25.

The atomizing assembly is disposed on the battery assembly. The first sealer 3 is disposed on the connector 4, and the connector 4 is disposed in the mouthpiece 2; the mouthpiece cover 1 is disposed on the mouthpiece 2; the joint 10 is disposed in the insulation ring 11, and the insulation ring 11 is disposed in the second fixed seat 13.

The second sealer 8 is disposed on the second fixed seat 13, and the regulating ring 12 is disposed on the second sealer 8. The seal ring 5 is disposed on and adapted to seal the first fixed seat 6; the screwed ring 7 is disposed in the first fixed seat 6; the first fixed seat 6 is disposed in the mouthpiece 2; the atomizing core 9 is disposed on the second fixed seat 13, and the second fixed seat 13 is connected to the first fixed seat 6.

The fourth sealer 30 is disposed on the sealing seat 31, and the sealing seat 31 is mounted on one end of the funnel 27; the third sealer 28 and the first spring 29 sleeve the funnel 27, and the funnel 27 is inserted in the e-liquid feeder 26; the e-liquid feeder 26 is disposed on the first fixed seat 6. When the atomizing core requires the e-liquid, press down the funnel 27, and then the e-liquid inlet of the funnel 27 is elastically opened and exposed out of the e-liquid feeder 26. The e-liquid is injected via the e-liquid inlet. After the injection, the funnel 27 is elastically withdrawn into the e-liquid feeder 26 and is sealed by the fourth sealer 30 and the sealing seat 31, and the e-liquid inlet is closely sealed in the e-liquid feeder 26, thus preventing the unwanted leakage of the e-liquid.

The regulating ring 12 comprises locating slots, and the second fixed seat 13 comprises stop pins corresponding to the locating slots stop pins. Under normal circumstances, rotating the regulating ring 12 can only regulate the volume flow rate of the vapor, and the atomizing core will not slide out. To replace the atomizing core, press down the regulating ring 12 to enable the locating slots to be clamped in the stop pins, and then rotate the regulating ring to screw out the old atomizing core.

The control plate 23 and the battery cell 25 are disposed at two sides of the support 24, respectively; the support 24 is disposed in the housing 22; the fifth sealer 18 and the second springs 20 are disposed on the output electrodes 19; the output electrodes 19 are disposed on the electrode holder 16 and are fixed by the fixed rings 21; the elastic sheets 15 are disposed on the electrode holder 16 and are fixed by the screws 14. The button 17 is disposed on the housing 22, and the electrode holder 16 is disposed in the housing 22.

The atomizing assembly communicates with the battery assembly via two elastic sheets 15 disposed at two sides of the battery assembly. The two elastic sheets 15 communicate with the first fixed seat 6 of the atomizing assembly. This simplifies the dismantling of the electronic cigarette and facilitates the replacement of the atomizing assembly. To dismantle the electronic cigarette, synchronously press the two elastic sheets 15 disposed at two sides of the battery cell, and then the atomizing assembly is ejected and detaches from the battery assembly, thus facilitating the replacement of the atomizing assembly. The battery cell is a built-in rechargeable battery cell. The electronic cigarette is lightweight and easy to carry.

It will be obvious to those skilled in the art that changes and modifications may be made, and therefore, the aim in the appended claims is to cover all such changes and modifications.

What is claimed is:

1. An electronic cigarette, comprising:
   an atomizing assembly, the atomizing assembly comprising a mouthpiece cover, a mouthpiece, a first sealer adapted to seal the mouthpiece, an atomizing core, a connector, a first fixed seat adapted to fix the atomizing core, a seal ring adapted to seal the first fixed seat, a screwed ring, a regulating ring, a second sealer adapted to seal the regulating ring, a joint, an insulation ring, a second fixed seat adapted to fix the regulating ring, an e-liquid feeder comprising an e-liquid inlet, a funnel, a third sealer adapted to seal the funnel, a first spring, a fourth sealer adapted to seal the e-liquid inlet of the e-liquid feeder, and a sealing seat; and
   a battery assembly, the battery assembly comprising screws, elastic sheets, an electrode holder, a button, output electrodes, a fifth sealer adapted to seal the output electrodes, second springs, fixed rings adapted to fix the output electrodes, a housing, a control plate, a support, and a battery cell;
wherein:
   the atomizing assembly is disposed on the battery assembly;
   the first sealer is disposed on the connector, and the connector is disposed in the mouthpiece; the mouthpiece cover is disposed on the mouthpiece;
   the joint is disposed in the insulation ring, and the insulation ring is disposed in the second fixed seat;
   the second sealer is disposed on the second fixed seat, and the regulating ring is disposed on the second sealer;
   the seal ring is disposed on and adapted to seal the first fixed seat; the screwed ring is disposed in the first fixed seat; the first fixed seat is disposed in the mouthpiece; the atomizing core is disposed on the second fixed seat, and the second fixed seat is connected to the first fixed seat;
   the fourth sealer is disposed on the sealing seat, and the sealing seat is mounted on one end of the funnel; the third sealer and the first spring sleeve the funnel, and the funnel is inserted in the e-liquid feeder; the e-liquid feeder is disposed on the first fixed seat;
   the regulating ring comprises locating slots, and the second fixed seat comprises stop pins corresponding to the locating slots;
   the control plate and the battery cell are disposed at two sides of the support, respectively; the support is disposed in the housing; the fifth sealer and the second springs are disposed on the output electrodes; the output electrodes are disposed on the electrode holder and are fixed by the fixed rings; the elastic sheets are disposed on the electrode holder and are fixed by the screws; and
   the button is disposed on the housing, and the electrode holder is disposed in the housing.

* * * * *